US010405887B2

(12) United States Patent
Davia

(10) Patent No.: US 10,405,887 B2
(45) Date of Patent: Sep. 10, 2019

(54) HANDHELD DEVICE FOR PERSONAL HYGIENE OF THE FOOT

(71) Applicant: GAJANANA, LLC, Suffolk, VA (US)

(72) Inventor: Paul C. Davia, Chesapeake, VA (US)

(73) Assignee: GAJANANA, LLC, Suffolk, VA (US)

( * ) Notice: Subject to any disclaimer, the term of this patent is extended or adjusted under 35 U.S.C. 154(b) by 379 days.

(21) Appl. No.: 15/355,743

(22) Filed: Nov. 18, 2016

(65) Prior Publication Data

US 2017/0164713 A1 Jun. 15, 2017

Related U.S. Application Data

(60) Provisional application No. 62/266,886, filed on Dec. 14, 2015.

(51) Int. Cl.
*A45D 29/20* (2006.01)
*A61B 17/54* (2006.01)
*A61M 35/00* (2006.01)
*A61B 17/00* (2006.01)

(52) U.S. Cl.
CPC .......... *A61B 17/54* (2013.01); *A61M 35/003* (2013.01); *A61B 2017/00473* (2013.01)

(58) Field of Classification Search
CPC ..... A61B 17/54; A61M 35/00; A61M 35/003; A61M 35/006; A45D 27/02; A45D 2200/1009; A45D 2200/1036; Y10T 16/473; A47K 7/026; A47K 7/028
USPC .......... 132/320; 15/143.1, 144.3, 210.1, 231, 15/233
See application file for complete search history.

(56) References Cited

U.S. PATENT DOCUMENTS

| | | | |
|---|---|---|---|
| 1,116,797 A | 11/1914 | Carmichael et al. |
| 1,446,344 A | 2/1923 | Graydon et al. |
| 3,531,814 A | 10/1970 | Safalow |
| 4,238,865 A | 12/1980 | Ingemann et al. |
| 4,877,018 A | 10/1989 | Ikebe et al. |

(Continued)

FOREIGN PATENT DOCUMENTS

| | | |
|---|---|---|
| EP | 0320131 A1 | 6/1989 |
| JP | H10323219 A | 12/1998 |
| JP | 2009050311 A | 3/2009 |

OTHER PUBLICATIONS

International Search Report and Written Opinion dated Feb. 24, 2017, issued in corresponding PCT/US2016/066133, 8 pages.

(Continued)

*Primary Examiner* — Rachel R Steitz
(74) *Attorney, Agent, or Firm* — Millen, White, Zelano & Branigan, P.C.; William Nixon

(57) ABSTRACT

A handheld device provides personal assistance for hygiene of the foot, toes, and toenails for persons unable to bend sufficiently at the waist to reach their feet. The handheld device includes a handle slat and a toe slat. The slats can rotate relative to each other using a hinge pin to extend to a length sufficient for a person to accomplish personal hygiene to the foot, toes, and toenails. The handle slat includes a handle to grasp the device. The toe slat includes an operating end having a thinner flat end to fit between toes and one or more corner balls to reach the interstitial space between and under the web connection of adjacent toes. A gauze applicator sock or tube covers the operating end to be used to perform actions for personal hygiene to the foot, toes, or toenails.

19 Claims, 11 Drawing Sheets

(56) References Cited

U.S. PATENT DOCUMENTS

| | | | |
|---|---|---|---|
| 4,961,733 A | 10/1990 | Joseph et al. | |
| 5,006,004 A | 4/1991 | Dirksing et al. | |
| 5,401,550 A | 3/1995 | Hannon | |
| 5,470,163 A | 11/1995 | Komala | |
| 5,560,068 A | 10/1996 | Blake | |
| 5,664,281 A * | 9/1997 | Pelfrey | A45D 34/04 15/144.1 |
| D398,155 S | 9/1998 | Latour et al. | |
| 5,842,488 A | 12/1998 | Belleau et al. | |
| 5,970,565 A | 10/1999 | Dubner | |
| 6,065,787 A | 5/2000 | Jarosch | |
| 6,126,217 A * | 10/2000 | Guadiana | B25B 9/00 294/24 |
| 6,340,026 B1 | 1/2002 | Shapiro | |
| 7,213,292 B1 | 5/2007 | Tucker | |
| D547,907 S | 7/2007 | Lawson et al. | |
| 7,310,850 B2 | 12/2007 | Ge | |
| D590,997 S | 4/2009 | Goldstein et al. | |
| 8,133,193 B2 | 3/2012 | Van Acker | |
| 2003/0000039 A1 | 1/2003 | Borcherds | |
| 2004/0107976 A1 | 6/2004 | Lawson et al. | |
| 2005/0059920 A1 | 3/2005 | Baril | |
| 2005/0200143 A1 | 9/2005 | Maestas | |
| 2005/0268416 A1 | 12/2005 | Sommers | |
| 2006/0075592 A1 * | 4/2006 | Sommers | A45D 34/04 15/244.1 |
| 2006/0130258 A1 * | 6/2006 | Ge | A47K 7/026 15/210.1 |
| 2006/0211978 A1 | 9/2006 | Do | |
| 2011/0035894 A1 | 2/2011 | Goldhammer | |
| 2011/0067195 A1 | 3/2011 | Oehler | |
| 2011/0230847 A1 * | 9/2011 | Malandruccolo | A61F 13/041 604/290 |
| 2014/0037363 A1 | 2/2014 | Sullivan et al. | |
| 2015/0026903 A1 | 1/2015 | Holley | |

OTHER PUBLICATIONS

English Abstract of JP2009050311, Publication Date: Mar. 12, 2009.
English Abstract of JPH10323219, Publication Date: Dec. 8, 1998.

* cited by examiner

HANDHELD DEVICE FOR PERSONAL HYGIENE OF THE FOOT

FIELD OF THE INVENTION

The present invention relates to a handheld device for personal hygiene of the foot, toes, and toe nails. More specifically, the present invention relates to a foldable handheld device that extends to reach the foot and toes of a user to allow access to the foot, toes, and toenails from standing, sitting, or reclining positions with minimal bending at the waist.

DISCUSSION OF THE RELATED ART

People having certain medical conditions, disabilities, recent surgery, or obesity are often not able to bend sufficiently at the waist to reach their feet in providing proper personal hygiene. Proper care of feet and toes is particularly important for diabetics to prevent potentially serious related medical complications. A device is needed to allow such people to personally attend to foot care, including washing and thorough drying between and under the toes, and application of medication, ointment, salve, cream or the like to the toes and toenails while in standing, sitting or reclining positions, requiring little bending at the waist. Current devices and applicators may not properly reach the feet with little bending at the waist and permit thorough washing, drying or medical care of the specific areas on, under and between the toes or as precisely on the toenails.

SUMMARY OF THE INVENTION

A handheld device for personal hygiene of the foot, toes, and toenails is disclosed that allows a person to accomplish proper hygiene of the toes and toenails from standing, sitting, or reclining positions with minimal bending at the waist. The device includes a handle slat at a proximal end of the device and a toe slat opposite the handle slat. The toe slat comprises an operating end having at least one corner ball located at a distal corner of the toe slat. The operating end includes a flat portion connected to the at least one corner ball. The device also includes a pivot portion connecting the handle slat and the toe slat to allow movement of the slats relative to each other. The device also includes a sock to cover the operating end and the at least one corner ball. Alternatively, a gauze applicator in a tube shape may be used to cover the operating end and the at least one corner ball. A preferred embodiment may include two corner balls, with one located at each of distal corner of the operating end.

A handheld device for interacting with interstitial spaces between toes also is disclosed. The device includes a handle slat having a handle. The device also includes a toe slat connected to the handle slat with a hinge pin and configured to rotate in relation to the handle slat such that the toe slat is opposite the handle slat in an extended position. The device also includes a first corner ball and a second corner ball located on an operating end of the toe slat. The corner balls fit within the interstitial spaces between the toes. The device also includes the operating end having a flat portion between the first corner ball and the second corner ball and an elongated portion extending away from the flat portion. The device also includes a fastener clip located in the toe slat on a side of the elongated portion of the operating end opposite the corner balls. The device also includes a sock, or a gauze applicator in a tube shape, to cover the operating end along the elongated portion. The sock or gauze application is held in place by the fastener clip.

An adjustable handheld personal hygiene device for a foot to dry between toes or to apply medicine, ointment, salve, cream, and the like to the foot, toes, or toenails also is disclosed. The device includes a handle slat having a handle. The device also includes a toe slat having an operating end and pivotally connected to the handle slat with a hinge pin. The device also includes a slide lock to cover the hinge pin when engaged with the handle slat and the toe slat. The device also includes the operating end having two corner balls separated by a flat portion such that the corner balls extend to the foot when the handle slat and the toe slat engage the locking mechanism. The device also includes a fastener clip located at an end of the operating end opposite the flat portion and embedded in the toe slat. The device also includes a sock to cover the operating end and the two corner balls. The sock is held in place by the fastener clip.

BRIEF DESCRIPTION OF THE DRAWINGS

Various other features and attendant advantages of the present invention will be more fully appreciated when considered in conjunction with the accompanying drawings.

DETAILED DESCRIPTION OF THE PREFERRED EMBODIMENTS

Figure 1:
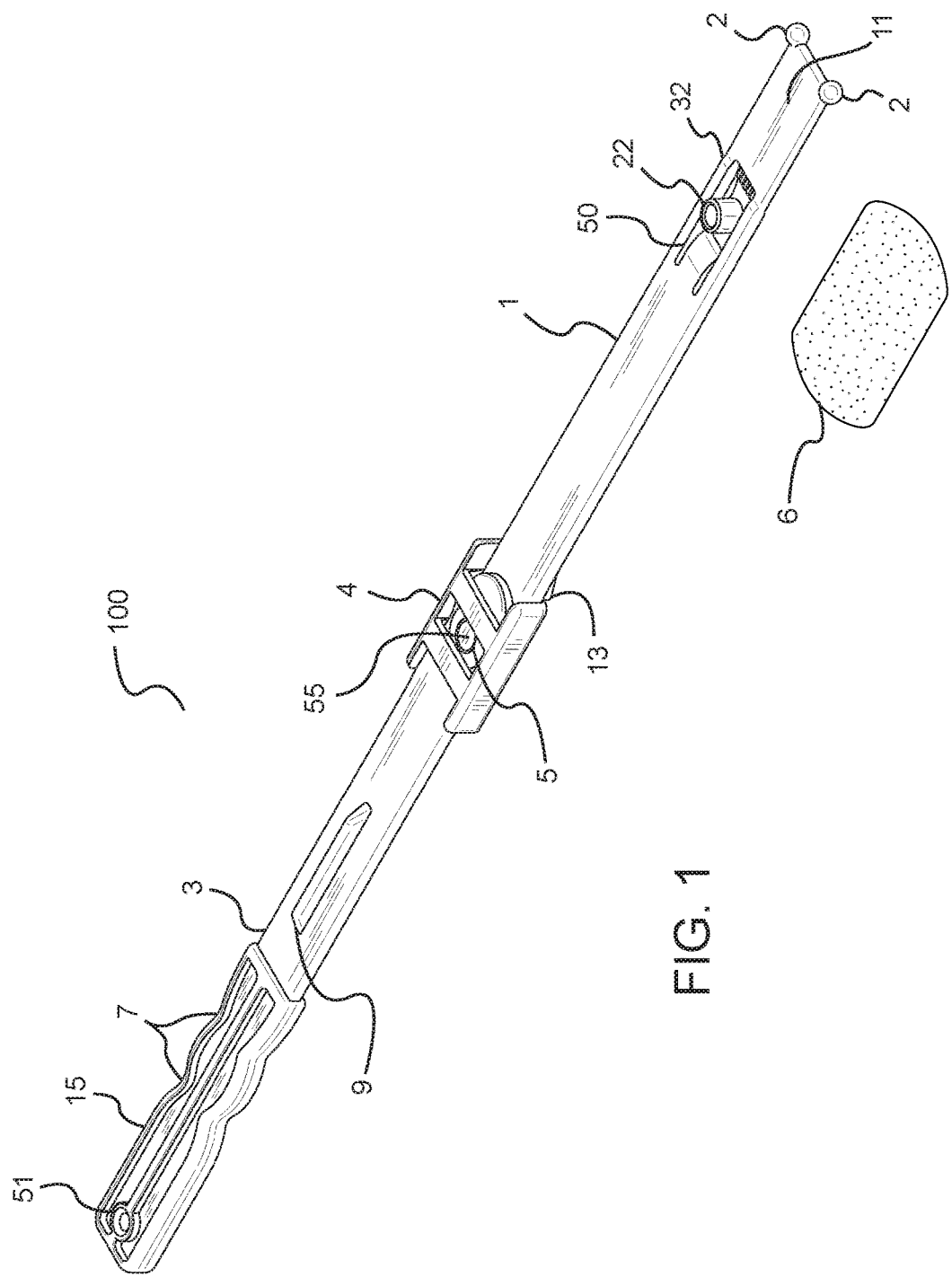
FIG. 1 illustrates a device in a locked position according to the disclosed embodiments.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 62/266,886 filed Dec. 14, 2015, are incorporated by reference herein.

Reference will now be made in detail to specific embodiments of the present invention. Examples of these embodiments are illustrated in the accompanying drawings. Numerous specific details are set forth in order to provide a thorough understanding of the present invention. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

The disclosed device includes a handheld personal hygiene device that extends from the hand of a user to interact with the user's foot, toes, and toenails. The disclosed embodiments allow persons who are unable to reach their feet to thoroughly dry between their toes or to apply medication, ointment, salve, cream, and the like between the toes and toe nails. These tasks are critical for many people, particularly those with diabetes, weight problems, recovering from surgery, or other condition that prevents one from bending at the waist to interact with their feet or toes.

The device includes slats that fold or shorten to provide compactness and convenience to the user for ease of storage. A small sock is attached at the operating end and moved down between each toe, for example, to dry between the toes or apply medicine. Alternatively, a gauze applicator sock or tube may be used to apply medication, ointment, salve, cream, and the like. The user may attach the sock or gauze applicator to the operating end using a fastener clip. The user may attach the sock to the toe slat, open and lock the device in the fully open position by sliding the slide lock over the hinge pin. The user grasps the handle and slides the operating end having the sock or gauze applicator attached thereto between the toes to wash, dry, or apply medication, ointment, salve, cream, and the like between the toes or to the toenails. The extended length allows ease of use while standing, sitting, or reclining with minimal bending at the waist.

For application of medication between the toes, the disclosed device will include a number of sterile or non-sterile disposable gauze tube-shaped material to which the medication, ointment, salve, cream, and the like is applied. The operating end of the disclosed device is designed to facilitate drying or medication application with the corner ball providing contact with the round interstitial, space located at the web connections under and between adjacent toes. For toenails, the corner balls also provide the user with a more precise control in applying medication, ointment, salve, cream, and the like on the gauze applicator by using a "dabbing" movement of the gauze-covered ball to the toenails.

When fully extended, the device is approximately 19-23 inches long. More particularly, the device may be about 21 inches long when fully extended. This length allows for drying between the toes or applying medication, ointment, salve, cream and the like to the toes or toe nails while standing, sitting, or reclining with minimal bending at the waist. The disclosed device may fold or configure itself into a variety of shapes to facilitate easy storage.

Figure 2:
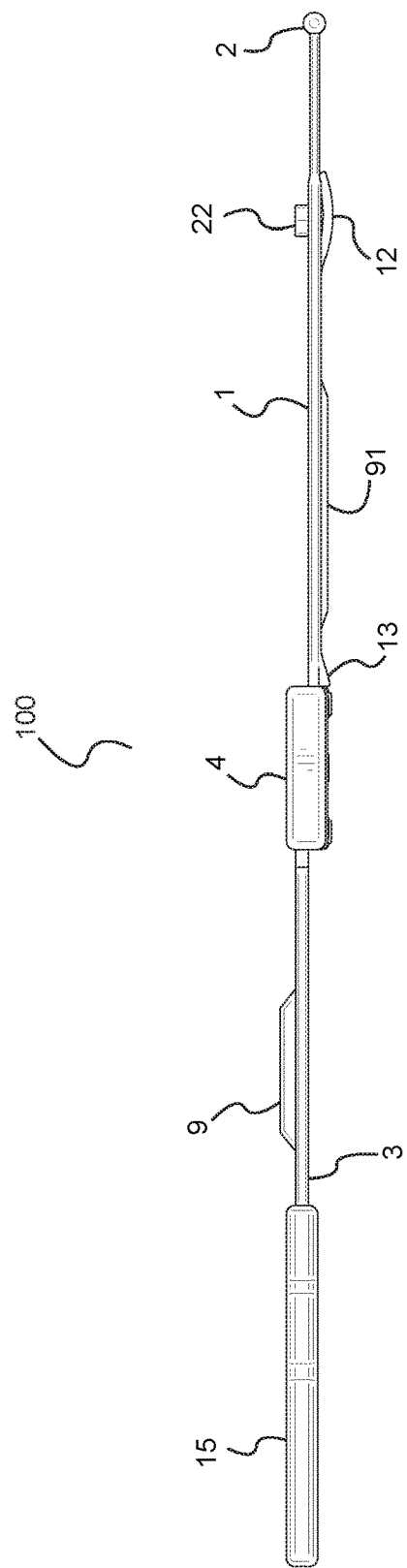
FIG. 2 illustrates a side view of the device in a locked position according to the disclosed embodiments.
Figure 3:
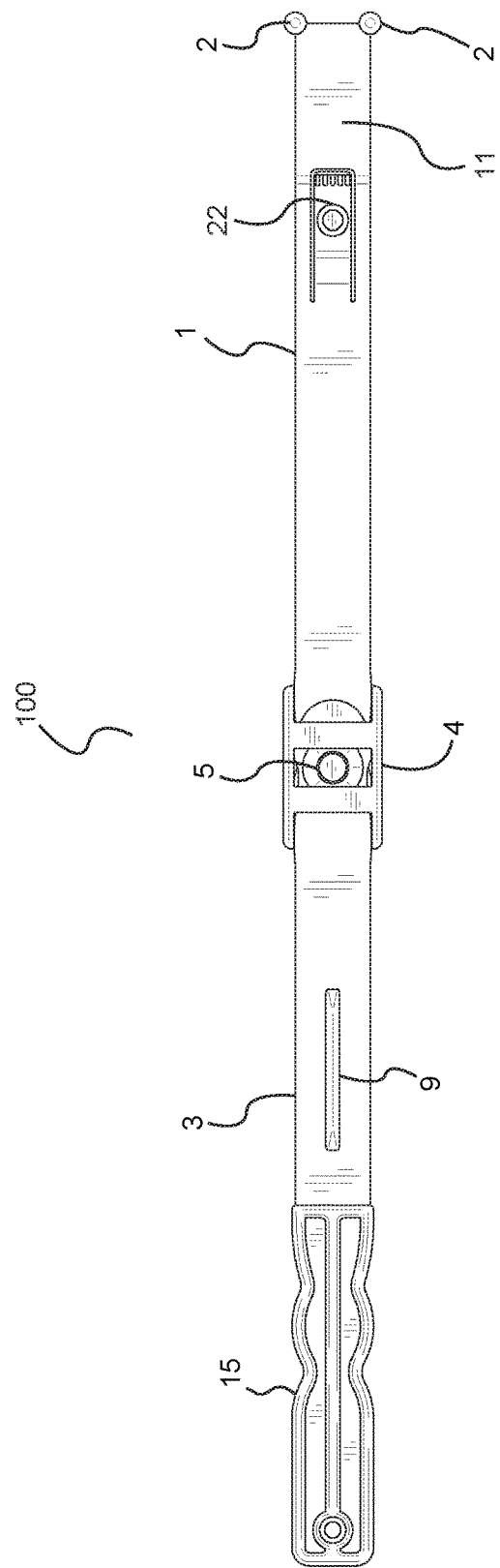
FIG. 3 illustrates a top view of the device in a locked position according to the disclosed embodiments.
Figure 4:
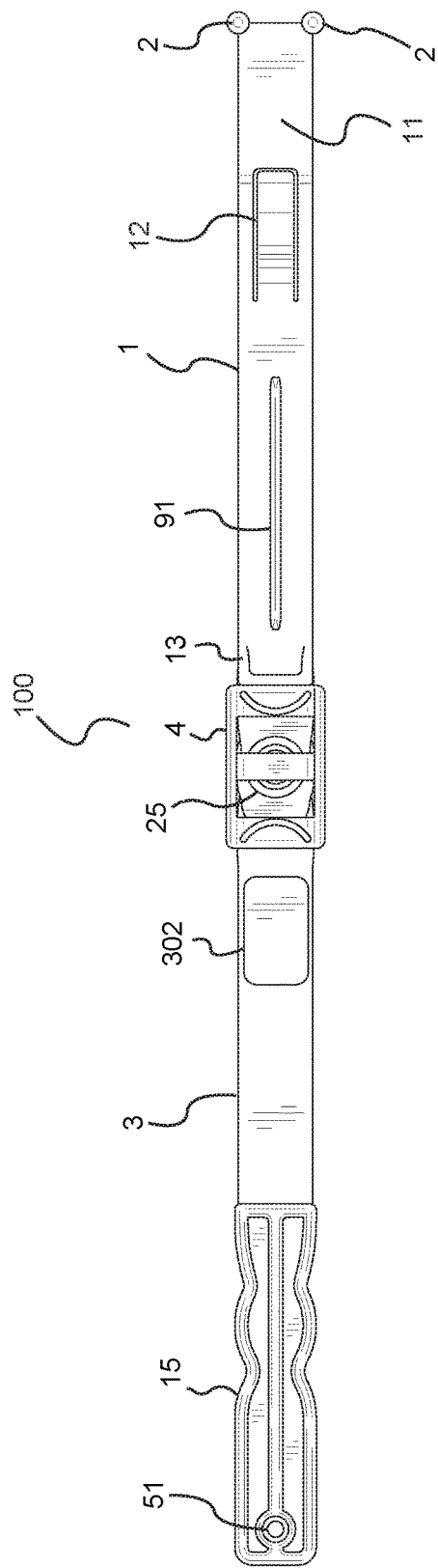
FIG. 4 illustrates a bottom view of the device in a locked position according to the disclosed embodiments.

FIG. 1 depicts a device 100 in a locked, or fully open, position according to the disclosed embodiments. FIG. 2 depicts a side view of the device in a locked position according to the disclosed embodiments. FIG. 3 depicts a top view of the device in a locked position according to the disclosed embodiments. FIG. 4 depicts a bottom view of the device in a locked position according to the disclosed embodiments. Device 100 is preferably made of rigid polymer or wood. If made of wood, then device 100 preferably is made of laminated polymer coated wood. Other materials may be used that allow for washing and cleaning of the surface after use.

The device 100 comprises a handle slat 3 and a toe slat 1, longitudinally oriented and connected. The toe slat 1 comprises at least one corner ball 2 located at an operating end 11. The operating end 11, using the least one corner ball 2, is adapted to be comfortably inserted between a user's toes. A corner ball 2 is a generally round body whose surface is adapted to fit into and conform to the round opening under the toes located at the interstitial space between adjacent toes. The device 100 can be moved in an up and down or back and forth motion to dry, massage or clean the interstitial space between the toes or any other foot surfaces such as the nail bed. The device may incorporate a washable or disposable absorbent portion 6 (e.g., a sock like structure) which is form-fitted over the operating end 11. In some embodiments, absorbent portion 6 may be a gauze, tube-shaped structure that stretches over the operating end 11 and corner balls 2.

Handle slat 3 may be rigid or semi-rigid. Handle slat 3 includes handle 15, which allows for a better grip when held by a user. Finger indents 7 provide additional gripping capability and allow patients with smaller or weaker hands to use device 100. Handle 15 may be comprised of soft plastic material that encompasses the far end of handle slat 3. Handle slat 3 also includes hanging hole 51 for storage of device 100 when not in use.

Handle slat 3 may include reinforcing ridge 9. Another reinforcing ridge 19 may be located on toe slat 1. Reinforcing ridges 9 and 19 are located longitudinally in the proximate center of handle slat 3 and toe slat 1, respectively. Preferably, ridges 9 and 19 are about 0.2 to 1.3 inches wide and about 0.12 to 0.15 inches high above the surface of the slats. Preferably, reinforcing ridge 9 of handle slat 3 is about 2 to 2.5 inches in length while reinforcing ridge 19 of toe slat 1 is about 4.5 to 5.5 inches in length. The reinforcing ridges provide strength and rigidity to slats 1 and 3 of device 100. Reinforcing ridge 9 also may serve to position slide lock 4, as disclosed below.

Device 100 may be comprised of any material which is rigid or semi-rigid and washable. Polymer materials, however, are preferred due to ease of cleaning and light weight. Metal or wood may also be used to construct either toe slat 1 or the handle slat 3.

In some embodiments, device 100 may be comprised of components that extend to be locked in an open position. FIGS. 1-4 show this position. Toe slat 1 and handle slat 3 are located longitudinally at opposite ends of each other. A hinge pin 5 is attached to toe slat 1 and handle slat 3 to allow the two slats fold, or laterally rotate, for ease of storage. Hinge pin 5 may include brass rivet 55 and stainless steel washer 25. Hinge pin 5 may attach to the slats through hinge pin holes in each having recessed openings to allow flush hinge pine surfaces.

Figure 5:
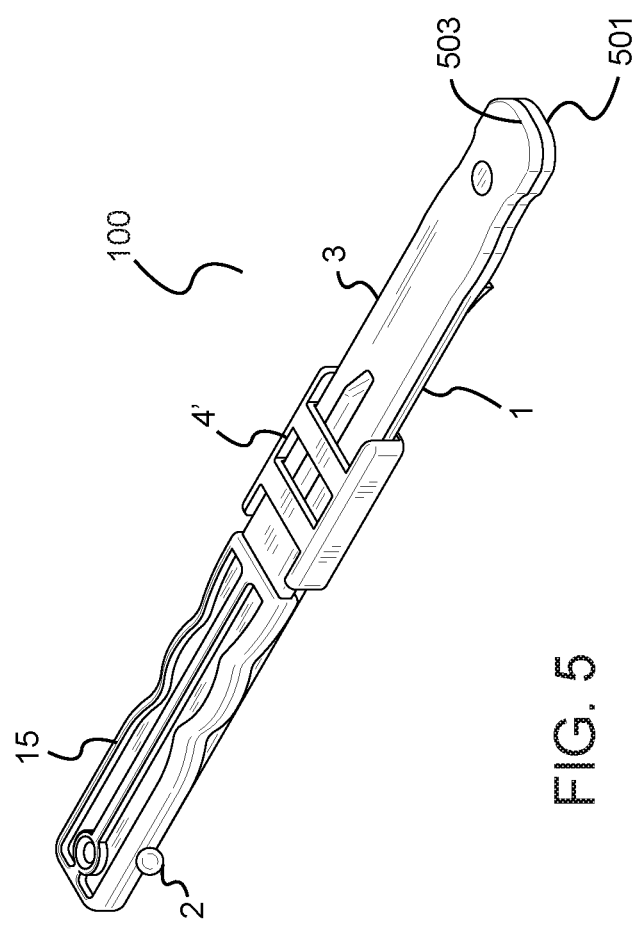
FIG. 5 illustrates a perspective view of the device in a folded position according to the disclosed embodiments.
Figure 6:
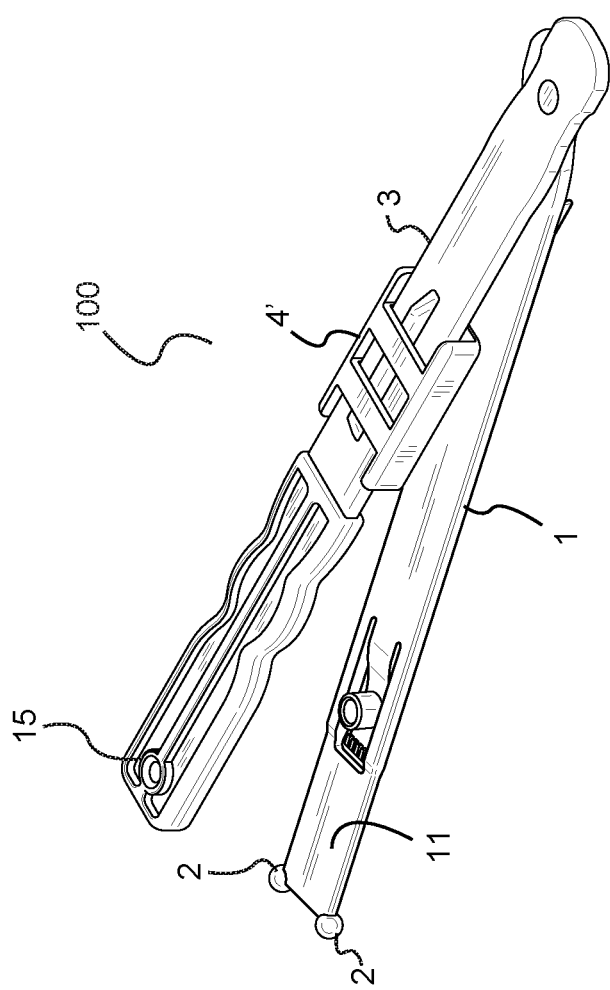
FIG. 6 illustrates a perspective view of the device in a partially folded position according to the disclosed embodiments.
Figure 7:
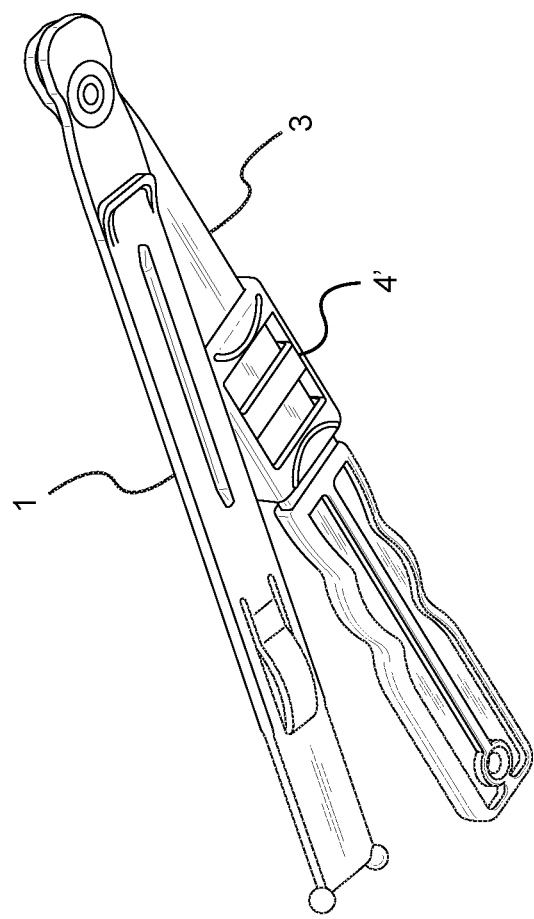
FIG. 7 illustrates another perspective view of the device in a partially folded position according to the disclosed embodiments.

In certain folding embodiments, such as those shown in FIGS. 5-7, one end of each slat is connected together at overlapping inner ends by hinge pin 5. Toe slat 1 may have overlapping inner end 501 while handle slat 3 includes overlapping inner end 503, thereby forming a "jack knife" configuration as shown in FIGS. 6 and 7, or a completed folded configuration as shown in FIG. 5. Corner balls 2 may be located under handle 15. When in the closed or locked configuration, overlapping inner ends 501 and 503 maintain contact via hinge pin 5.

As shown, slide lock 4 moves along handle slat 3 depending on what configuration is desired. If one wants to place device 100 in the locked, or open, position, then slide lock 4 is placed over hinge pin 5 until slide lock component 906 reaches slide lock stop 13. Slide lock 4 may be positioned by hand or thumb back and forth along handle slat 3. As shown in FIGS. 5-7, slide lock 4 may be moved to a position (shown as 4') that allows the slats to rotate relative to each other around hinge pin 5.

When moved from position 4' to the one showed for slide lock 4, slide lock 4 places device 100 into the fully extended and locked position. Slide lock 4 may be prevented from sliding beyond overlapping ends 501 and 503 by slide lock stop 13. Slide lock stop 13 is shown on one side of toe slat 1, but may be included on both sides in some embodiments. Preferably, slide lock stop 13 is located on the bottom of toe slat 1 and about 0.9 to 1.5 inches from the center of hinge pin 5 toward operating end 11. This distance, however, may vary. The bottom of toe slat 1 may be defined as the side having reinforcing ridge 91.

Figure 9:
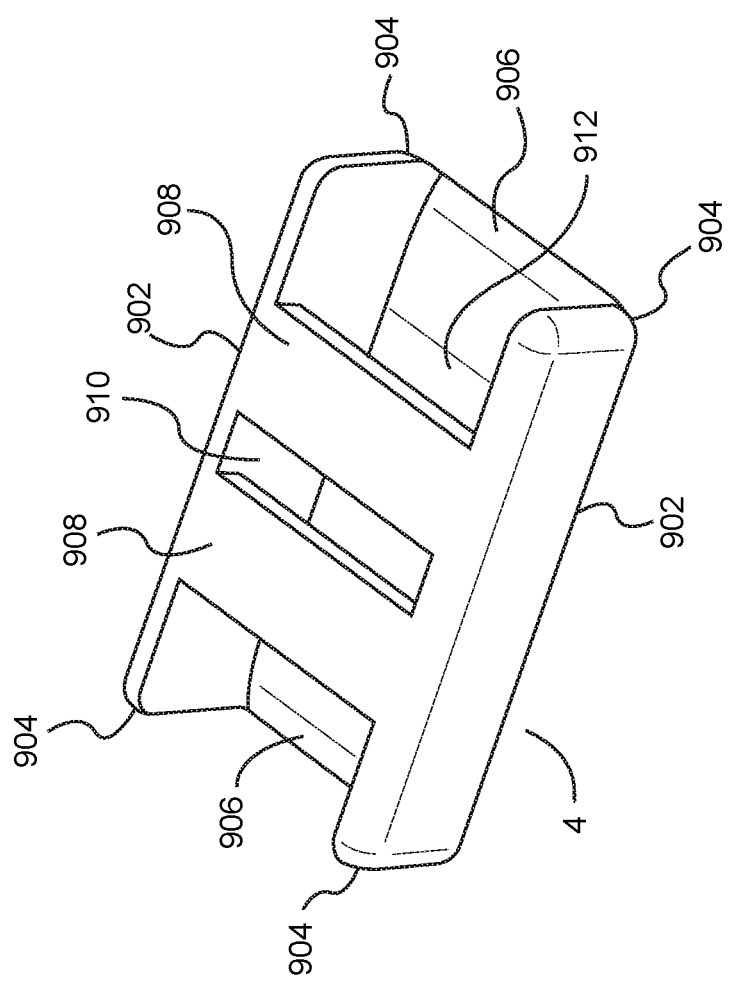
FIG. 9 illustrates a slide lock according to the disclosed embodiments.

An example of a slide lock 4 may be shown by FIG. 9. Slide lock 4 includes portions and holes that allow one to determine the position of the slide lock 4 on device 100. For example, one would like to know when slide lock 4 is positioned above hinge pin 5, even though slide lock stop 13 provides some reference. Slide lock 4 includes sides 902 that each includes ends 904. Preferably, ends 904 are curved for easy movement using a thumb or finger. Sides 902 may be rounded as well for easy use. Bottom portions 906 attach to sides 902 underneath slats 1 and 3. Bottom portions 906 may slope downwardly to the ends of slide lock 4 for easy movement. Top portions 908 also attach to sides 902, but above slats 1 and 3. Top portions 908 also are located inwards from bottom portions 906. This configuration allows for easy movement of slide lock 4 using a finger or thumb. Top portions 908 are separated by hole 910. Hole 910 allows one to determine the position of slide lock 4 on device 100. Bottom portions 906 are separated by hole 912, which also allows one to view where slide lock 4 is. Preferably, hole 912 is larger than hole 910.

To lock device 100 in a fully open position, handle slat 3 and toe slat 1 are rotated to a fully open length. Slide lock 4 is moved from handle slat 3, as shown by position 4', by thumb or hand over hinge pin 5. Slide lock 4 is moved until it touches slide lock stop 13 located on toe slat 1. The edge of bottom portion 906 abuts with slide lock stop 13 when device 100 is in the fully open position. When in position 4', slide lock 4 may ride up on reinforcing ridge 9 using sides 902 to position the slide lock closer to handle slat 3. This allows toe slat 1 to more easily fold under handle slat 3 for storage when not in use.

In some embodiments, toe slat 1 is generally from 0.5 to 1.5 inches wide. Preferably toe slat 1 is between 0.7 to 1.3 inches wide. Most preferably, toe slat 1 is between 0.9 to 1.1 inches wide. In some embodiments, toe slat 1 is generally from 0.09 to 0.3 inches thick. More preferably, toe slat 1 is between 0.10 to 0.2 inches thick. Most preferably, toe slat 1 is between 0.11 to 0.15 inches thick. In embodiments where toe slat 1 and handle slat 3 fold, the length of folded device 100 is generally between 9-14 inches long and, preferably, between 10-13 inches long.

Figure 8:
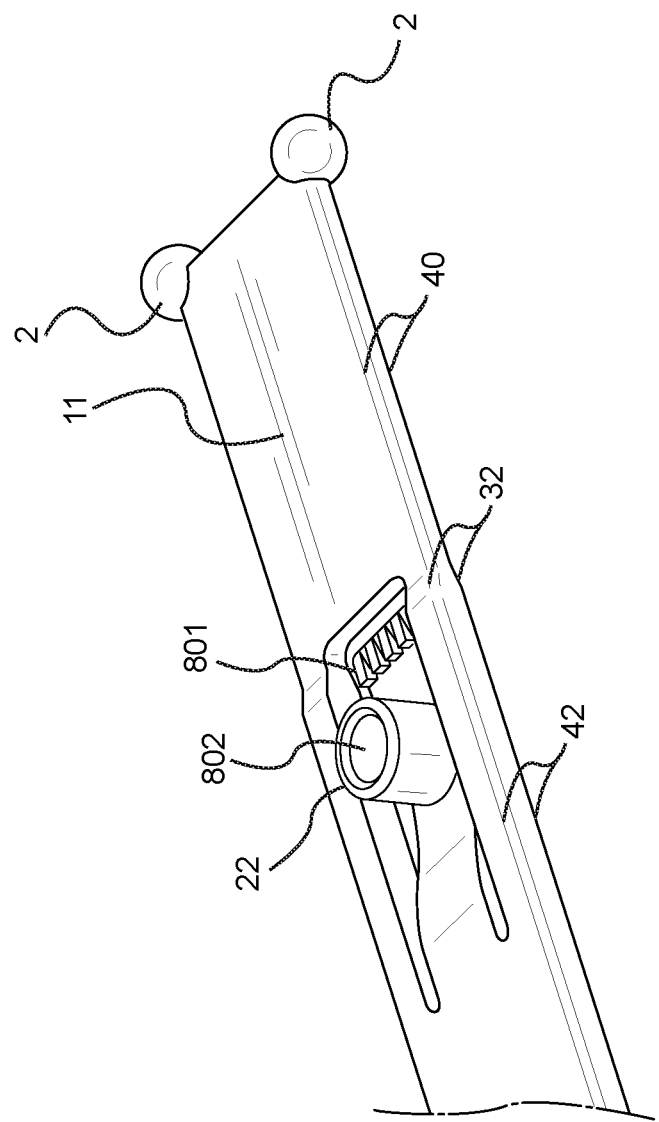
FIG. 8 illustrates a close up view of the operating end of the toe slat according to the disclosed embodiments.

The distal end of toe slat 1 contains operating end 11 having at least one corner ball 2 integral with the tip of the most distal end corner of toe slat 1. This may be disclosed in greater detail by FIG. 8. Preferably, toe slat 1 contains two corner balls 2. Operating end 11 is the portion of device 100 which fits between the toes of the user. Operating end 11 extends between the corner balls 2 and extends to fastener clip 12, as can be seen in FIGS. 4 and 8. In a preferred embodiment, thickness 40 of operating end 11 of toe slat 1 is thinner than thickness 42 of toes slat 1 above the operating end 11. Sloping portion 32 may separate these two sections such that it slopes inwardly to thickness 40. Sloping portion 32 may be aligned with fastening clip 12 so that sock 6 covers the entire area of operating end 11. Teeth 801 also may be seen, and are fashioned to grasp the open end of the sock or gauze being used by device 100. Fastener push button 22 may be depressed to allow entry of the sock edge between teeth 801 to hold it in place upon release of the fastener push button. The reduced thickness for operating end 11 allows better manipulation of device 100 between the toes. The thicker width of the rest of toe slat 1 provides greater rigidity to the toe slat during use.

At least one corner of operating end 11 has a generally smooth, approximately 0.2 to 0.3 inch diameter corner "ball" 2 formed integral with the corner. In some embodiments, both corners of operating end 11 comprise a corner ball 2. Corner ball 2 gives an appearance as a spherical shape at each side of operating end 11. The shape generally conforms to and facilitates drying beneath and between the toes at the round interstitial spaces formed at the underside web connection between adjacent toes. To facilitate insertion between toes, operating end 11 of toe slat 1 may be fashioned with thinner material (e.g., 0.065 to 0.095 inches, preferably 0.07 to 0.085 inches and most preferably 0.075 to 0.08 inches thick), shown as thickness 40 disclosed above.

Corner balls 2 may have an approximately spherical body (e.g., round like a typical ball) or a slightly irregular spherical body (e.g., an ellipsoidal shape). Corner balls 2 may each be of the same size or, alternatively, may differ in size. In some embodiments, corner balls 2 are of different diameter and differing spheroid shapes. One's foot comprises smaller toes and big toe. Because the interstitial space between one's big toe is generally slightly larger than the space between the adjacent toes, two corner balls 2 may be of different diameter and/or shape to accommodate the different toe spaces. In some embodiments, a corner ball 2 is generally from 0.18 to 0.4 inches in diameter. More preferably, a corner ball 2 is between 0.15 to 0.3 inches in diameter. Most preferably, a corner ball 2 is between 0.2 to 0.28 inches in diameter.

To place device 100 into a closed position, slide lock 4 may be moved back to position 4'. Preferably, slide lock 4 is moved over reinforcing ridge 9 of handle slat 3. This allows overlapping ends 501 and 503 to rotate operating end 11 towards handle 15 for compact storage or packaging. This compactness allows a user to more easily carry device 100.

Absorbent portion 6 of device 100 may be formed from an absorbent material such as a nonwoven fabric, a woven fabric, cotton or other similar material. The material may be in the form of a sock like structure shown in FIG. 1, which completely encompasses operating end 11 of toe slat 1 or as a tube shape fabric or gauze being open at each end. The absorbent material functions to wash or thoroughly dry between toes after a shower or bath. In some embodiments, absorbent material 14, or sock 6, may contain a soap or pharmacological active agent which is mixed, infused, or impregnated into the fibers of the absorbent portion. Alternatively, absorbent material may be in the form of a gauze sock or tube, which is attached to one or both sides of operating end 11. The absorbent material 14 may also function to apply medication, ointment, salve, cream, or the like, to the area between toes to the toenails. Absorbent portion 6 may be disposable or reusable/washable. The absorbent material may be smooth or the material may have a coarse outside surface to facilitate cleaning and/or scrubbing. The absorbent material can be made of one of a range of materials and or surface textures depending on the intended use of the invention device. A relatively smooth and thin absorbent material (such as a single layer of cotton fabric) may be used to lightly cleanse or apply essential or massage oils to the inter-toe surfaces.

Absorbent portion 6 may be formed from cotton or polymer fabric and bear short bristles or a similar scrubbing surface for cleaning the inter-toe surfaces more deeply. Absorbent portion 6 can be in the form of a sock like structure which is adapted to be pulled on and off toe slat 1 in the same manner as a human would apply or remove a sock from their foot. Alternatively, gauze portion 14 may be in a tube shape, open at each end and may be used by sliding one open end over operating end 11 and corner balls 2. Absorbent portion 6 or gauze portion 14 is attached via fastener 50 adjacent to operating end 11 of toe slat 1 to prevent absorbent portion 6 or gauze portion 14 from becoming dislodged during use.

A soft, raised fabric surface can be incorporated into absorbent portion 6 if formed from terrycloth, a material well known in washcloths and towels to dry feet and between the toes after shower or bath.

In alternative embodiments, absorbent portion 6 may be replaced by a gauze portion 14 in the form of a sock or tube in a manner as previously described for absorbent portion 6. Gauze portion 14 (shown in FIG. 10) accepts and allows placement of medication, ointment, salve, cream, or the like, which is then placed between the toes or to the toe nails for medical treatment such as fungal infection. Gauze portion 14 may be sterile or non-sterile.

Absorbent portion 6 or gauze 14 may be fastened to operating end 11 by any suitable fastener 50. Such fasteners may include, but not limited to, clips, hook and fastener material, spring loaded fasteners, adhesive strips, snaps, or other similar fastening devices. Fastener 50 needs to have sufficient clamping or adhering force such that absorbent portion 6 or gauze portion 14 is retained during the use of device 100.

In a preferred embodiment, fastener 50 includes a fastener clip 12 along with a finger push button 22 to open the fastener clip such that absorbent portion 6 or gauze portion 14 may slide under the clip to be held in place by teeth 801 when the button is released. Fastener 50 may be located inward towards hinge pin 5 from operating end 11. Fastener 50 borders operating end 11 to hold absorbent portion 6 or gauze portion 14 in place. Fastener clip 12 is separated from toe slat 1 and bends downwardly. Finger push button 22 extends upward from fastener clip 12 to allow one to push it downwards to place or remove absorbent portion 6. Finger push button 22 may be circular and include a hollow portion 802 to facilitate placement of a finger or thumb to press down on fastener clip 12. As shown in FIG. 8, fastener clip 12 also includes teeth 801 that grip and hold in place absorbent portion 6 or gauze portion 14. Thus, absorbent portion 6 or gauze portion 14 may be placed within fastener clip 12 for use with device 100, and then removed by pressing down finger push button 22.

Referring back to FIGS. 1-4, device 100 includes handle 15 on handle slat 3. Handle 15 may be its own section comprising material different than the remainder of handle slat 3 In some embodiments, handle 15 may cover that portion of handle slat 3 and be comprised of closed cell foam, viscoelastic foam, or a rubber-like material, or any material that is soft and easy to grip. Handle 15 may be form fitted. Hanging hole 51 is located at the distal end of handle slat 3 and includes the hole in handle 15. Hanging hole 51 facilitates hanging device 100 on a hook, when not in use.

Device 100 is preferably made of rigid polymer or laminated plastic coated wood. Any material which is rigid and washable is contemplated. However, polymer materials are preferred due to ease of cleaning and light weight. Metal or wood may also be used to construct handle slat 3. Particularly, preferred materials are high density polyethylene, polypropylene, polycarbonate, acrylonitrile-butadiene copolymers and the like. Injection molded polymers are particularly preferred. Preferably, handle slat 3 is made of the same material as toe slat 1 and may be cleaned or sterilized without causing damage. In some embodiments, slide lock 4 is moved from the locked position over hinge pin 5 over and onto reinforcing ridge 9 and against handle slat 3. Reinforcing ridge 9 moves slide lock 4 up, via bars 908, to allow toe slat 1 to flat and overlap slide lock 4 and handle slat 3 when device is fully folded and not in use, as shown in FIG. 5.

Figure 10A:
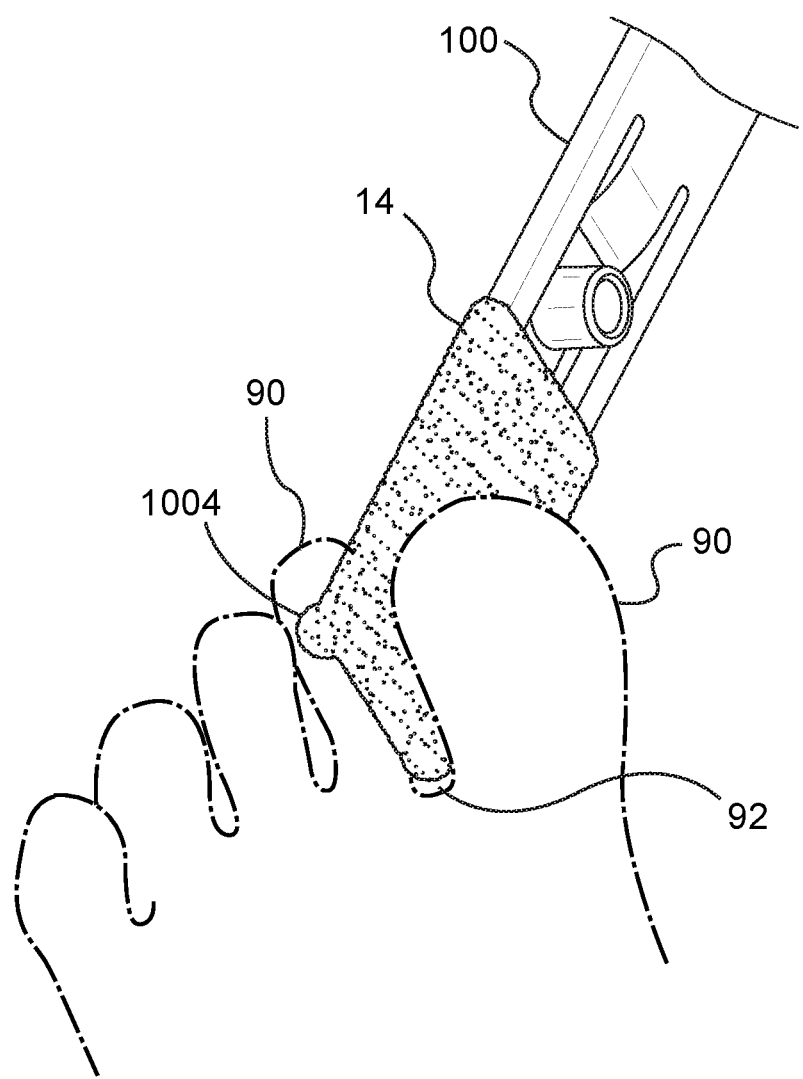
FIG. 10A illustrates use of the device between toes according to the disclosed embodiments.
Figure 10B:
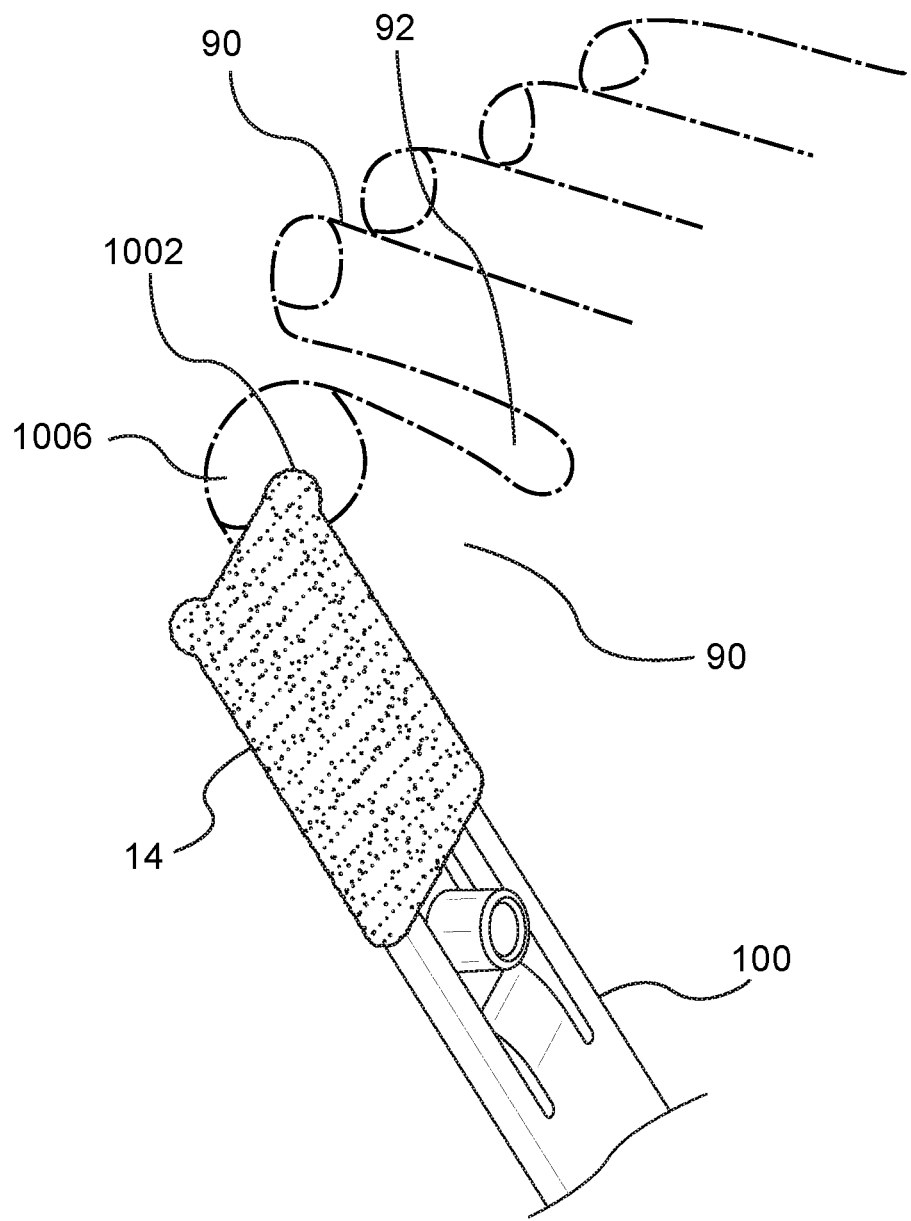
FIG. 10B illustrates use of the device on a toe nail according to the disclosed embodiments.

FIGS. 10A and 10B depict an application of medicine 1002 to foot 90 using device 100 according to the disclosed embodiments. FIGS. 10A and 10B show the use of gauze 14 to apply medication, ointment, salve, cream, and the like, shown as 1002. FIG. 10A depicts use of device 100 between toes 90. FIG. 10B depicts the use of device 100 on toe nail 1006. Gauze portion 14 may be sterile or non-sterile. In some embodiments, absorbent portion, or sock, 6 may be used. Device 100 is inserted between toes 90 so that medication 1002 is applied to space 92 between toes 90. As shown, one toe 90 may be the big toe. End 1004 depicts the point where corner balls 2 meet gauze portion 14. Preferably, end 1004 is pulled tight so that one may apply pressure when corner ball 2 meets toes 90 or space 92. Further, end 1004, and, therefore, corner ball 2 fits within space 92. End 1004 also may be used to engage toe nail 1006. Corner ball 2 provides the support to fit between toe 90 and toe nail 1006 for the application of medicine 1002 or to dry that area. Corner ball 2 also may access the part of toe nail 1006 under toe nail 1006. This may occur using a "dabbing" motion.

Thus, device 100 allows one to perform personal hygiene on feet and toes with limited bending or use of hands to directly perform these actions. People having disabilities, injuries, or other conditions that prevent bending at the waist to use their hands to conduct personal hygiene can benefit from the use of device 100. The arrangement of the components disclosed above allows one to reach spaces and portions between and beneath toes. Device 100 may be used to wash, dry, and apply medication, ointment, salve, cream, and the like, with limited bending at the waist. Device 100 restores independence to people who are physically unable to perform this important care of feet and toes. These features are not available from known personal hygiene devices. Device 100 also is easily stored and cleaned.

It will be apparent to those skilled in the art that various modifications to the disclosed may be made without departing from the spirit or scope of the invention. Thus, it is intended that the present invention covers the modifications and variations disclosed above provided that these changes come within the scope of the claims and their equivalents.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A handheld device for personal hygiene of the foot, toes and toenails, the device comprising:
   a handle slat at a proximal end of the device;
   a toe slat opposite the handle slat, the toe slat comprising an operating end having two corner balls located at distal corners of the toe slat, wherein the operating end includes a flat portion extending along the toe slat to the distal corners and extending between the two corner balls;
   a hinge pin connecting the handle slat and the toe slat to allow movement of the slats relative to each other;
   a locking mechanism to cover the hinge pin to lock the handle slat and the toe slat into an extended position; and
   a sock or tube to cover the operating end and the two corner balls.

2. The handheld device of claim 1, wherein a length of the flat portion extends longitudinally along the toe slat.

3. The handheld device of claim 1, wherein the further comprising a locking mechanism holds the handle slat and the toe slat in a rigid extended position.

4. The handheld device of claim 3, wherein the locking mechanism includes a slide lock to cover the hinge pin to configure the handle slat and the toe slat together in the rigid extended position.

5. The handheld device of claim 3, wherein the locking mechanism is located on the handle slat when disengaged to allow the toe slat and the handle slat to rotate laterally to each other for compact storage.

6. The handheld device of claim 1, wherein the hinge pin is located in apertures within the handle slat and the toe slat.

7. The handheld device of claim 1, further comprising a fastener clip in the toe slat to hold the sock or tube onto the operating end and to cover the at least one corner ball.

8. The handheld device of claim 7, wherein the fastener clip includes a finger push button to move teeth to an open position to grasp or release the sock or tube.

9. The handheld device of claim 7, further comprising a sloping portion between the fastener clip and the operating end.

10. The handheld device of claim 1, wherein a thickness of the operating end is less than a thickness of the remainder of the toe slat.

11. The handheld device of claim 1, wherein the handle slat includes a handle.

12. A handheld device for interacting with interstitial spaces between toes and to a surface of the toenails, the device comprising:
   a handle slat having a handle;
   a toe slat connected to the handle slat with a hinge pin and configured to rotate in relation to the handle slat such that the toe slat is opposite to and longitudinally aligned with the handle slat in an extended position;
   a locking mechanism to cover the hinge pin to lock the handle slat and the toe slat into the extended position;
   a first corner ball and a second corner ball integrally located at corners on an operating end of the toe slat, wherein the corner balls fit within the interstitial spaces located between and under a web connection of adjacent toes;
   the operating end having a flat portion extending between the first corner ball and the second corner ball and an elongated portion extending to a fastener clip;
   the fastener clip located in the toe slat opposite the corner balls; and
   a sock or tube to cover the operating end along the elongated portion and held in place by the fastener clip.

13. The handheld device of claim 12, further comprising a reinforcing ridge on a side of the toe slat.

14. The handheld device of claim 12, wherein the fastener clip includes a finger push button.

15. The handheld device of claim 12, wherein the operating end has a thickness less than a thickness of the remainder of the toe slat.

16. The handheld device of claim 12, further comprising a sloping portion between the fastener clip and the operating end.

17. An adjustable handheld personal hygiene device to wash, dry, or apply medicine to parts of a foot, the device comprising:
   a handle slat having a handle;
   a toe slat having an operating end and pivotally connected to the handle slat with a hinge pin;
   a locking mechanism to cover the hinge pin when engaged to prevent movement of the handle slat and the toe slat in relation to each other;
   the operating end having two corner balls spaced apart and connected by a flat portion such that the corner balls extend to the foot and toes when the handle slat and the toe slat are engaged by the locking mechanism in an open and extended position;
   a fastener clip embedded in the toe slat and located opposite the flat portion; and
   a sock or tube to cover the operating end and the two corner balls, wherein the sock is held in place by the fastener clip.

18. The adjustable handheld personal hygiene device of claim 17, wherein the handle slat and the toe slat move relative to each other using the hinge pin when the locking mechanism is disengaged with the slat.

19. The adjustable handheld personal hygiene device of claim 17, wherein the locking mechanism includes a slide lock that moves along an area of the handle slat when disengaged.

* * * * *